United States Patent
Faust

(10) Patent No.: US 10,918,528 B2
(45) Date of Patent: Feb. 16, 2021

(54) HEAD SUPPORT DEVICE

(71) Applicant: Wayde Faust, Los Angeles, CA (US)

(72) Inventor: Wayde Faust, Los Angeles, CA (US)

( * ) Notice: Subject to any disclaimer, the term of this patent is extended or adjusted under 35 U.S.C. 154(b) by 675 days.

(21) Appl. No.: 15/628,526

(22) Filed: Jun. 20, 2017

(65) Prior Publication Data

US 2017/0360203 A1 Dec. 21, 2017

Related U.S. Application Data

(60) Provisional application No. 62/352,985, filed on Jun. 21, 2016.

(51) Int. Cl.
*A47G 9/10* (2006.01)
*A61G 13/12* (2006.01)
*A61F 13/12* (2006.01)

(52) U.S. Cl.
CPC ............ *A61F 13/12* (2013.01); *A47G 9/1009* (2013.01); *A61G 13/121* (2013.01); *A47G 9/10* (2013.01); *A61G 13/12* (2013.01)

(58) Field of Classification Search
CPC ...... A47G 9/10; A47G 9/1009; A47G 9/1045; A47G 9/1054; A47G 9/1063; A47C 7/38; A47C 7/383; A47C 20/02; A47C 20/026; A61G 13/12; A61G 13/121; A61G 13/1215; A61F 13/12
USPC ................ 5/636–638, 640, 643, 632, 622
See application file for complete search history.

(56) References Cited

U.S. PATENT DOCUMENTS

| | | | | | |
|---|---|---|---|---|---|
| 2,634,435 | A | * | 4/1953 | Budd | A47G 9/1009 132/333 |
| 2,803,022 | A | * | 8/1957 | Wynkoop | A61F 5/01 5/632 |
| 3,241,160 | A | * | 3/1966 | Escobar | A47C 7/66 5/418 |
| 3,337,883 | A | * | 8/1967 | Allison | A47G 9/1009 5/638 |
| 3,403,413 | A | * | 10/1968 | Calhoun | A47G 9/1009 5/638 |
| 3,608,103 | A | * | 9/1971 | Seid | A47C 20/026 5/661 |
| 4,045,678 | A | * | 8/1977 | Rickard | A61B 6/0421 378/174 |
| 4,063,318 | A | * | 12/1977 | Nicholson | A47G 9/1045 5/656 |
| 4,504,050 | A | * | 3/1985 | Osborne | A61G 13/12 378/179 |
| 4,641,883 | A | * | 2/1987 | Kato | A47G 9/1045 297/118 |
| 4,828,321 | A | * | 5/1989 | Harper | A47G 9/1009 297/188.2 |
| 5,337,429 | A | * | 8/1994 | Tucker | A45D 19/04 4/516 |

(Continued)

*Primary Examiner* — Robert G Santos

(57) ABSTRACT

Provided is a device for supporting a person's head in a horizontal position when the person is standing, walking or sitting in an erect position, comprising: a) a support member configured to be positioned above the head and further configured to be attached (wearable) to the person's body; b) a head rest configured to be attached to the support member, the head rest configured for a person to rest the person's forehead upon, whereupon the weight of the head is transferred from the neck to the support member, relieving strain on the neck muscles of the person and allowing for mobility.

1 Claim, 7 Drawing Sheets

(56) References Cited

U.S. PATENT DOCUMENTS

| | | | | |
|---|---|---|---|---|
| 5,551,110 A * | 9/1996 | Armstrong | ............ | A47G 9/1009 |
| | | | | 135/121 |
| 6,151,734 A * | 11/2000 | Lawrie | ................. | A47C 20/026 |
| | | | | 5/622 |
| 8,555,439 B2 * | 10/2013 | Soto | ..................... | A61G 13/121 |
| | | | | 128/869 |
| 2012/0124747 A1 * | 5/2012 | Soto | ..................... | A61G 13/101 |
| | | | | 5/622 |
| 2017/0360203 A1 * | 12/2017 | Faust | ........................ | A61F 9/00 |
| 2018/0353806 A1 * | 12/2018 | Brask | ................. | A63B 21/4003 |
| 2019/0053647 A1 * | 2/2019 | Sakamoto | ............ | A47G 9/1009 |
| 2020/0037752 A1 * | 2/2020 | Davenport | ........... | A61G 13/126 |

* cited by examiner

HEAD SUPPORT DEVICE

CROSS-REFERENCE

The present application claims the benefit of U.S. provisional patent application No. 62/352,985 filed on Jun. 21, 2016, which is incorporated herein by reference in its entirety.

BACKGROUND SECTION OF THE INVENTION

Patients that receive vitrectomy surgery (for macular hole, or for macular pucker or for detached retina) and have a gas bubble or oil bubble placed in the eye to maintain pressure against the retina, have to keep their heads in a horizontal, face down position looking to the ground for up to a two week or more recovery period. It is virtually impossible for someone to hold their head in a face down position while standing or walking for more than a few minutes without experiencing neck and upper-back pain. There is a need in the art for a device to help these patients by providing neck pain relief and mobility during the face down recovery period.

SUMMARY SECTION OF THE INVENTION

Figure 1:
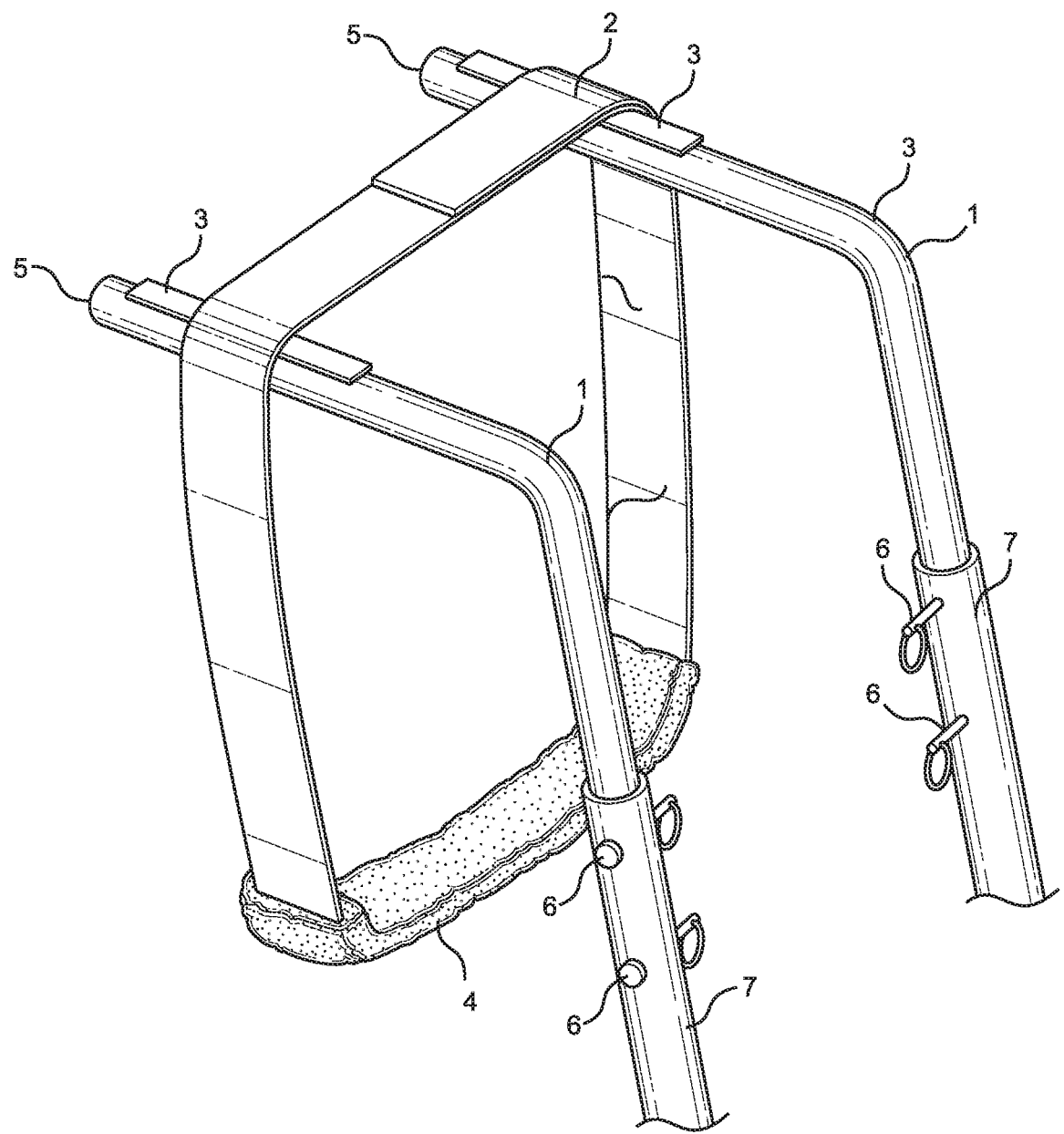
FIG. 1 illustrates a device for supporting the head in a horizontal direction according to first embodiment.

Provided is a device for supporting a person's head in a horizontal position when the person is standing, walking or sitting in an erect position, comprising: a) a support member attached to the person's body and configured to be positioned above the head; b) a head rest attached to the support member, the head rest configured for a person to rest the person's forehead; wherein a person walks with the device configured to be attached to the person's body and rests the forehead on the head rest. The head rest can be a strap attached to the support member. The strap can have a width of 1.5 inches to 2.5 inches, such as 2 inches. The support member can be on both left and right sides of the person's head, and the strap is attached to the support member on each side of the person's head. The support member can be configured in various shapes such as L-shaped, C-shaped, D-shaped, or U-shaped. The device can further comprise a securing member that is configured to be positioned behind the person through which the support member is configured to be attached to the body. The securing member can be a backpack frame with two bars on top that keep the support member in position. Each bar of the securing member can receive a post, for a total of two posts, and the posts are pivotally attached to the support member. The device can further comprise a stopper placed in front of the posts and below the support member, the stopper limiting range of movement of the support member. The device can further comprise a crossbar connecting the securing member to the support member. Two crossbars can be used, each crossbar attached to one bar of the securing member. Each bar of the securing member can have a plurality of openings configured to receive a hook at one end of the crossbar. The securing member can be attached to the body through one or more of a shoulder harness or a hip belt.

Provided is a device for supporting a person's head in a horizontal position when the person is standing in an erect position, comprising: a) a securing member configured to be attached to the body, the securing member having up to two bars; b) a support member attached to the securing member and configured to be positioned above the head; c) a head rest attached to the support member, the head rest configured for a person to rest the person's forehead; wherein a person walks with the device attached and rests the forehead on the head rest. The securing member can be a backpack frame with one or more of a shoulder harness and a hip belt. The two bars of the securing frame can be parallel to each other. The device comprises one or more posts, each post configured to be attached to the securing member at one end and attached to the support member at another end. The device can further comprise a stopper placed in front of the posts and below the support member, the stopper limiting range of movement of the support member. The support member can be L-shaped, D-shaped, C-shaped, or U-shaped. The two crossbars can be used, each crossbar attached to one bar of the securing member.

Provided is a device for supporting a person's head in a horizontal position when the person is standing in an erect position, comprising: a) a securing member configured to be attached to, a person, the securing member having two bars; b) two posts, each post configured to be attached to one of the bars of the securing member; c) a support member attached to the two posts and configured to be positioned above a the head of the person; d) a head rest attached to the support member, the head rest configured for a person to rest the person's forehead; e) one of i) a stopper placed in front of the posts and below the support member, the stopper limiting range of movement of the support member; ii) two crossbars, each crossbar connecting the securing member or the post to the support member, wherein a person rests the forehead on the head rest and is able to walk around while wearing the device.

DETAILED DESCRIPTION OF THE INVENTION

The present invention provides for a device that allows for patients who have undergone vitrectomy surgery to walk around while their head is supported in a horizontal position. The device, in supporting the head, transfers the weight of the head to the backpack thereby relieving the strain on the neck muscles from holding the head in a horizontal position. The device allows these patients to be able to stand and walk around and sit erect while keeping their heads secured in a horizontal position, providing a respite from having to sit or lay motionlessly still with their head facing the ground during the up to two week recovery period.

The device is a flexible, adjustable device that can be added onto the top of a backpack frame. This device allows a patient to comfortably support their head at the prescribed horizontal angle by relieving resulting pain from pressure upon the neck and upper back by transmitting the weight of the head from the neck and upper back to the backpack which in turn is supported by the much stronger shoulders and hips.

The device can be comprised of a flexible, padded, adjustable loop, cradling the head of the user comfortably around the forehead. Said loop is adjustably attached to a fixed intermediate section which attaches to the top of a conventional hiking backpack frame. Keeping the forehead in a horizontal position, the device securely and comfortably cradles the forehead and transmits the force applied by the head of the user to the users shoulders and hips. This device alleviates any resultant overwhelming pain that would otherwise reside in the neck and upper back from trying to maintain the head in a horizontal face down position over any length of time. The cradling loop can keep the head "locked" in the face down position and helps prevent the user from moving their head from side to side.

Provided is a head support device configured to maintain the head of an individual in a face down position, preferably in a substantially parallel position relative to the ground. The head support devices comprises a support member 1 configured to position a strap 2 attached to the support member for holding a forehead of a person in the down position, the strap 2 generally located below or at about chin level and in front of the person when the person is in an upright (erect) position, and a securing member 7 for attachment to the person and the support member 1, the securing member 7 securing the device to the person.

The support member 1 can be positioned above and to the side of the user's head, allowing the strap to drop from above and sides of the user to below chin of the user. The securing member 7 is worn by the person. The securing member 7 can be a frame of a backpack, for example a rigid structure that is placed against the back and is secured to the body through straps. The backpack would then have a complementary securing member 7 for receiving the support member 1. The support member 1 can be attached adjustably and/or reversibly to the securing member 7.

FIG. 1 illustrates one embodiment of the device where support member 1, here in the shape of L beams, is connected to securing member 7. Support member 1 is complementary to the ends of securing member 7, and is connected with a pin 6 or a fastener through complementary openings that align. Support member 1 can have a portion that is substantially vertical (0 to 25 degrees forward) and/or in the same direction of the end of securing member 7, and then bend towards front of the user so that strap 2 can be positioned in front of the user. Length of strap 2 can be adjusted by a user. As illustrated in FIG. 1, two support members 1 are used, each fabricated from a single piece of material. Strap 2 is supported by a substantially horizontal portion of support member 1. Strap 2 can be attached to the supporting member 1 with the use of attaching member 3, such a Velcro® (such as hook-and-loop fastener), or alternatively be made to loop around support member 1 without use of attaching member 3. Strap 2 can have padding 4 at point of contact of the forehead of a person with strap 2, and be configured to receive the forehead of a person in a substantially horizontal position. Support member 1 can have an end cap 5 for an aesthetic look. The device can easily be made flat for storage and shipping. When pins 6 are removed, support member 1 can be rotated in relation to securing member 7 to obtain a flat package, and additional complementary openings can allow securing them in this position.

Figure 2:
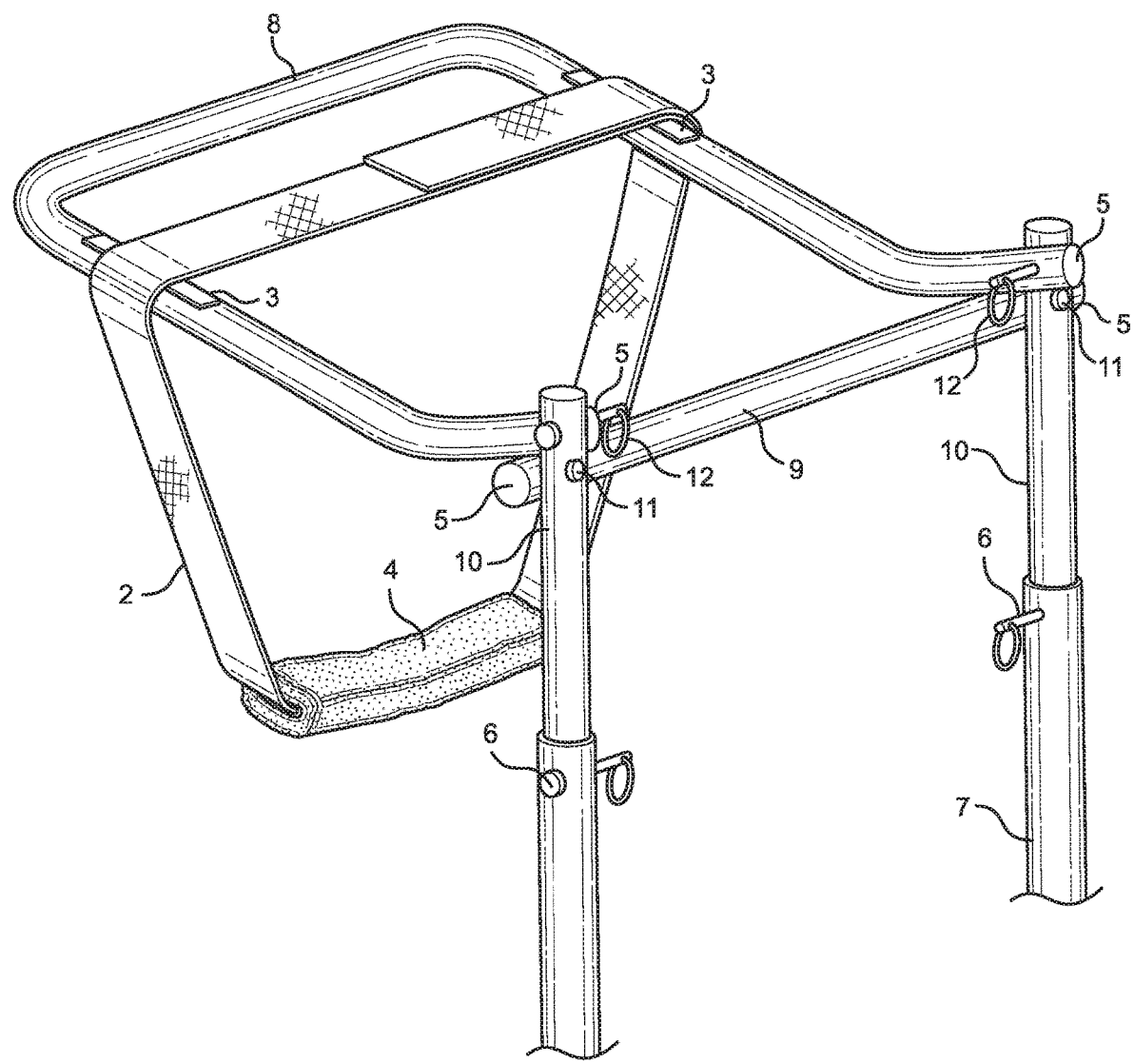
FIG. 2 illustrates a device for supporting the head in a horizontal direction according to a second embodiment.
Figure 5:
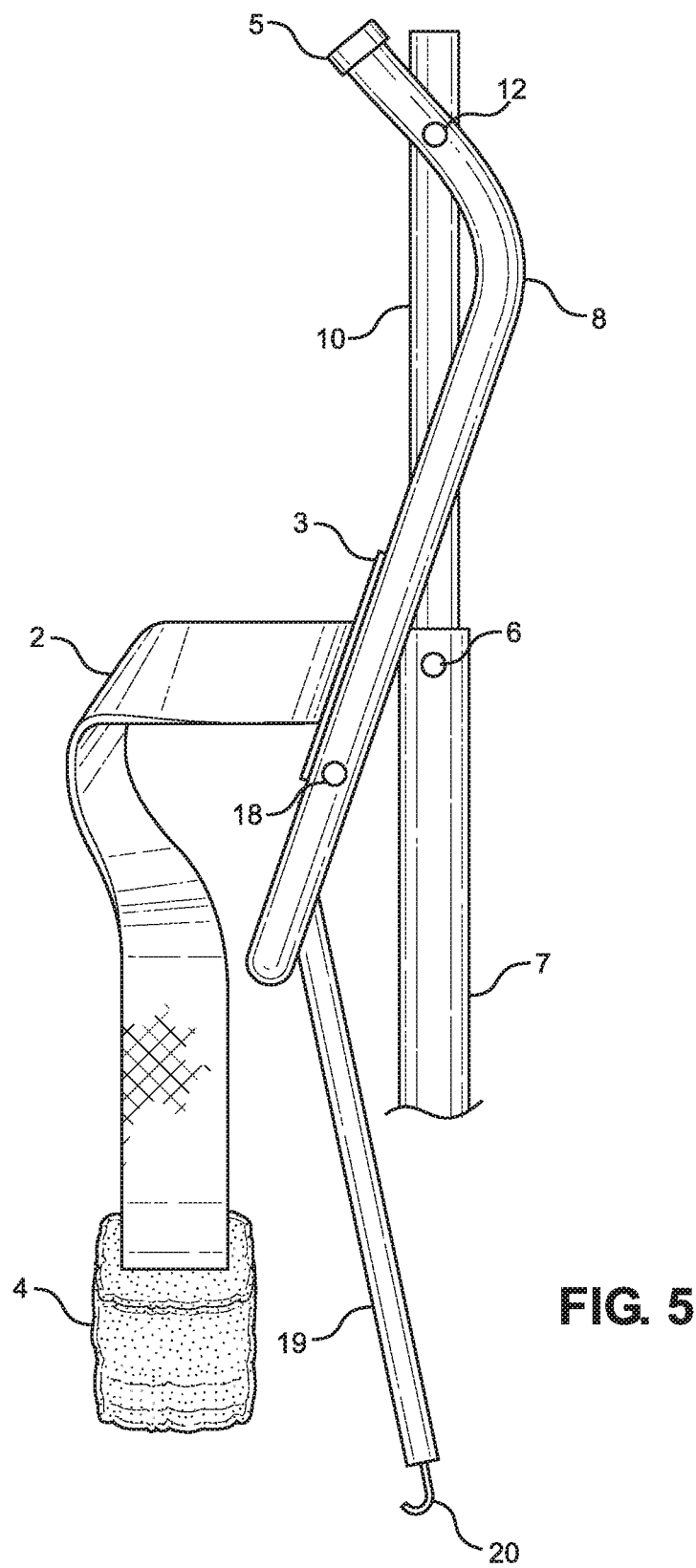
FIG. 5 illustrates the device of FIG. 3 in a stowed position.

FIG. 2 illustrates a perspective view of another embodiment similar to that of FIG. 1. In this embodiment, securing member 7 receives posts 10, which can be detachably attached to each other with a pin 6 or another fastener. Support member 8, here in the shape of a ring with two ends (C, D or U-shaped), is made from a single piece of material and is attached to each post 10 with the fastener or a pin 12. Support member 8 can be configured to pivot. Pivoting range of support 8 can be stopped by stopper 9, which can be any shaped member attached with fastener 11 to post 10 that limits range of pivoting. As illustrated in FIG. 5, the stopper 9 is in shape of a bar that is attached in a transverse or perpendicular direction to each post 10, and is positioned below the attachment point of support 8 to post 10. Stopper 9 stops member 8 from touching a person's head and positions member 8 above a person's head. Strap 2 can be attached in a similar manner as provided for the first embodiment.

Support 8 can be pivoted towards back of securing member 7, allowing for a substantially flat device that can be stored and shipped easily.

Figure 3:
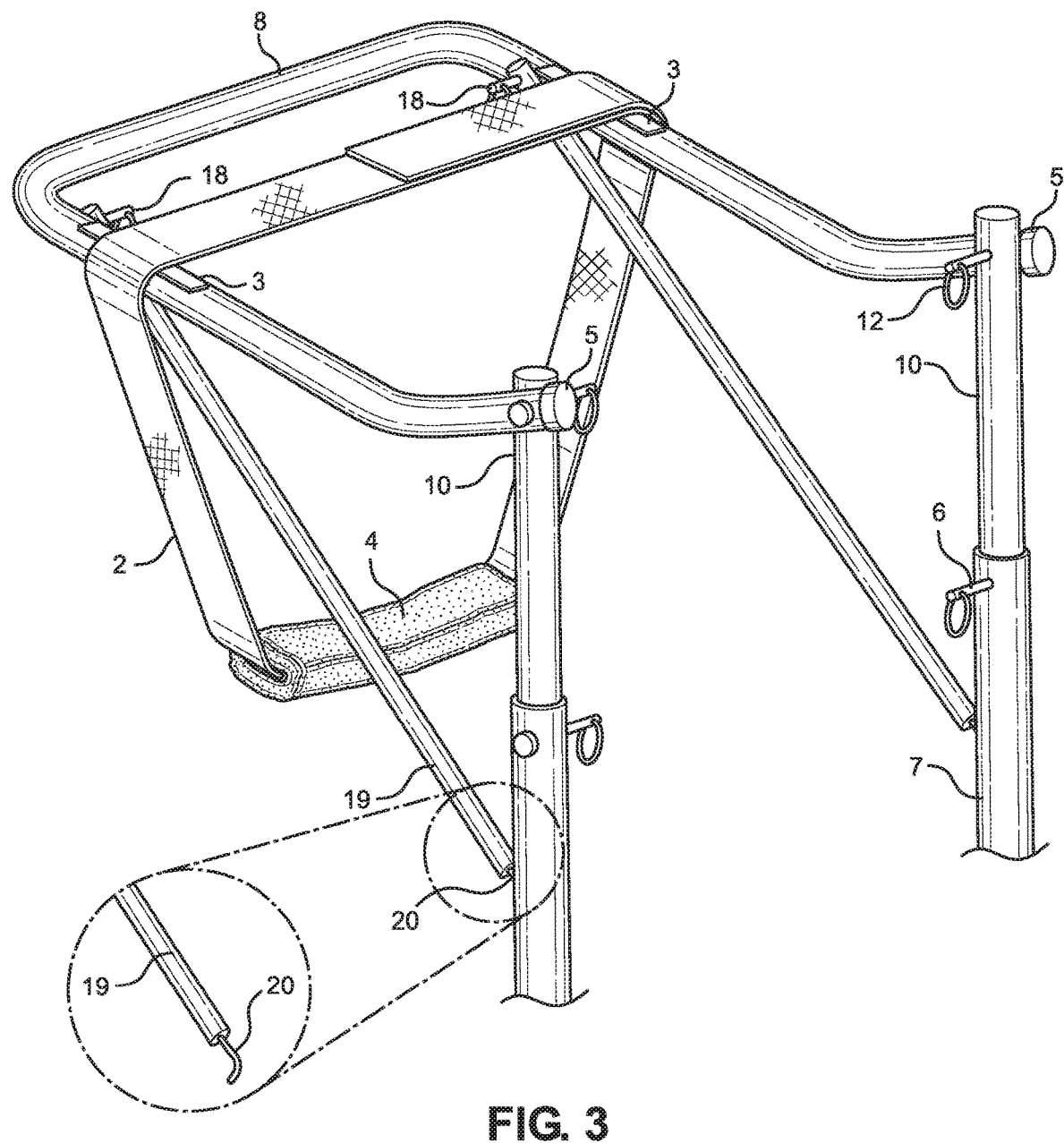
FIG. 3 illustrates a device for supporting the head in a horizontal direction according to a third embodiment.

FIG. 3 illustrates another embodiment of the device that is similar to the device of FIG. 2. In this embodiment, stopper 9 is not used. Instead of stopper 9, a crossbar 19 is used to attach support member 8 to securing member 7. Crossbar 19 can be attached to inside portion of support member 8 and front of securing member 7. Crossbar 19 can have a hook 20 that goes inside of an opening in securing member 7. The other side of crossbar 19 can be attached to support member 8 with a fastener, such as pin 18.

Figure 4:
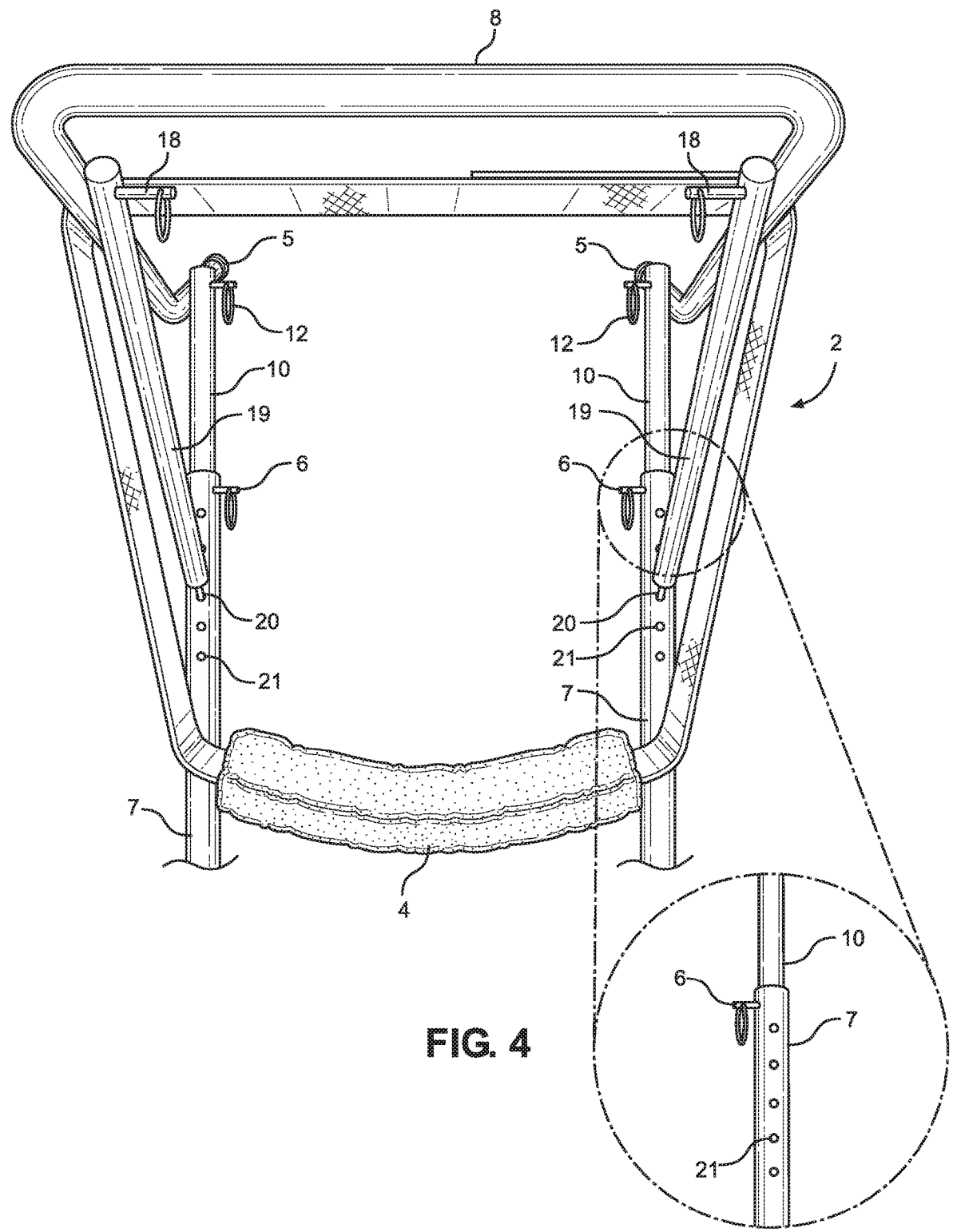
FIG. 4 illustrates a top view of the device of FIG. 3.

FIG. 4 is another view of the device illustrated in FIG. 3. Visible in this view are the openings 21 on securing member 20. Hook 20 of cross-member 19 is placed in one of these openings 21. The plurality of openings 21 allow for adjusting the height of securing member 8 and ultimately the device.

FIG. 5 illustrates storing the device of FIG. 3 (stowed position). By removing hook 20 of crossbar 19 from openings 21, the device collapses into a stowed position that can be shipped and stored easily.

Figure 6:
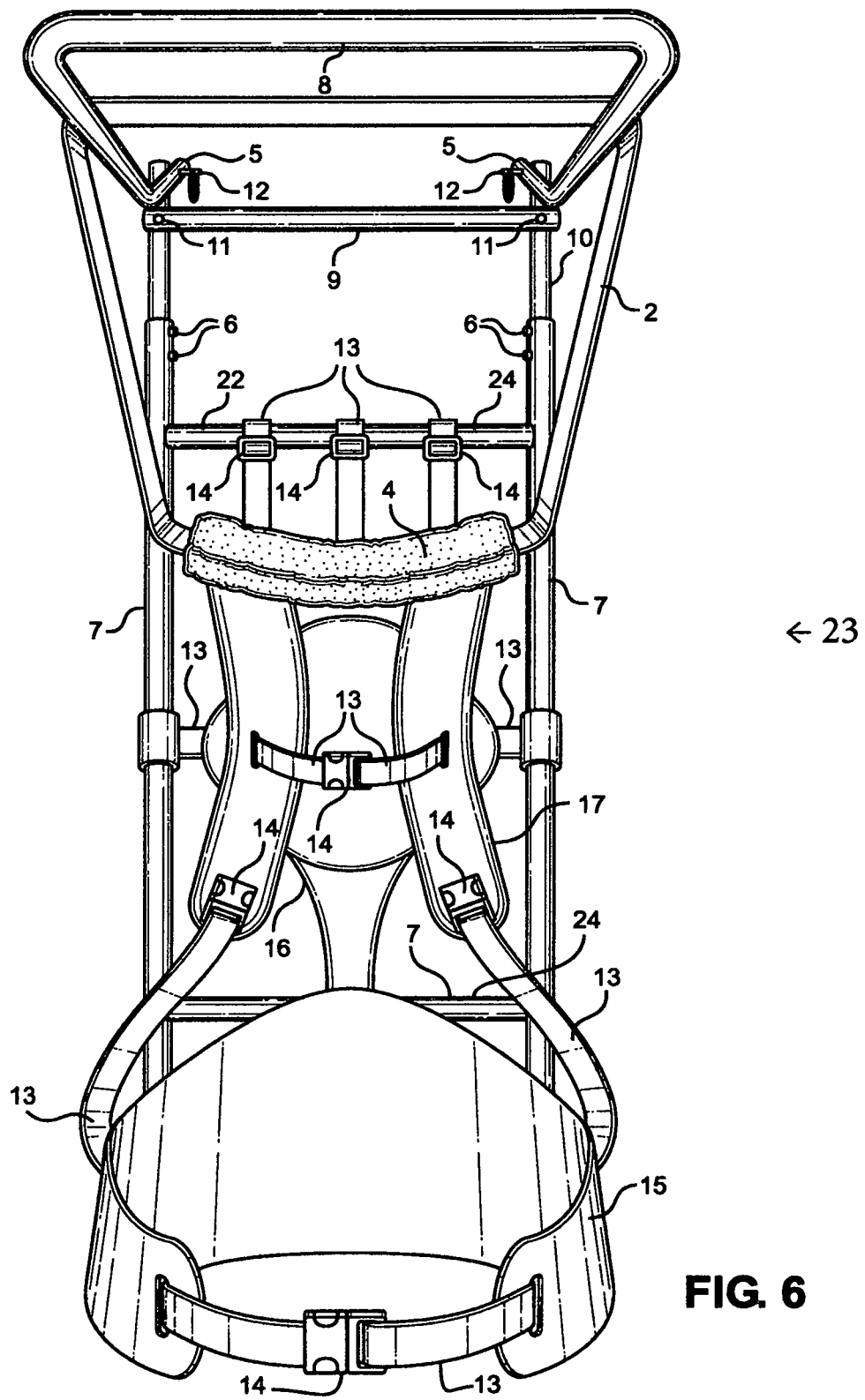
FIG. 6 illustrates the device of FIG. 2 attached to a backpack frame. The devices of all the embodiments can be configured to be similarly attached to a backpack frame.

FIG. 6 illustrates a backpack support structure 23. The support structure 23 can be any structure that is configured to be attached to the body of the user, and is configured to be attached to and secure the support member 1 (or 8) to which the strap 2 is attached. The backpack support structure 23 includes the securing member 7, which can be two substantially upright and parallel structures (rods, bars, tubing) of a rigid material, such as aluminum, metal, plastic, or wood dowel. The two securing members 7 can be joined to each other, such as with a bar, rod, or tubing in a transverse direction 24 that is attached to both structures. Backpack shoulder harnesses 13 are then attached, such as to one or more of the bars in transverse direction 24, so that a person can secure the device to the body. In addition to resting on a person's shoulder, support structure 23 can be attached to a person's hip with padded hip belt 15. Support structure 23 can also have adjustable straps 13; slide release buckles 14, back pad 16, and shoulder harness 17. Shoulder harness 17 can be used to secure the securing member 7 to the back of a person, with the straps holding securing member 7 in the same manner in which a backpack is held on a person's back.

Figure 7:
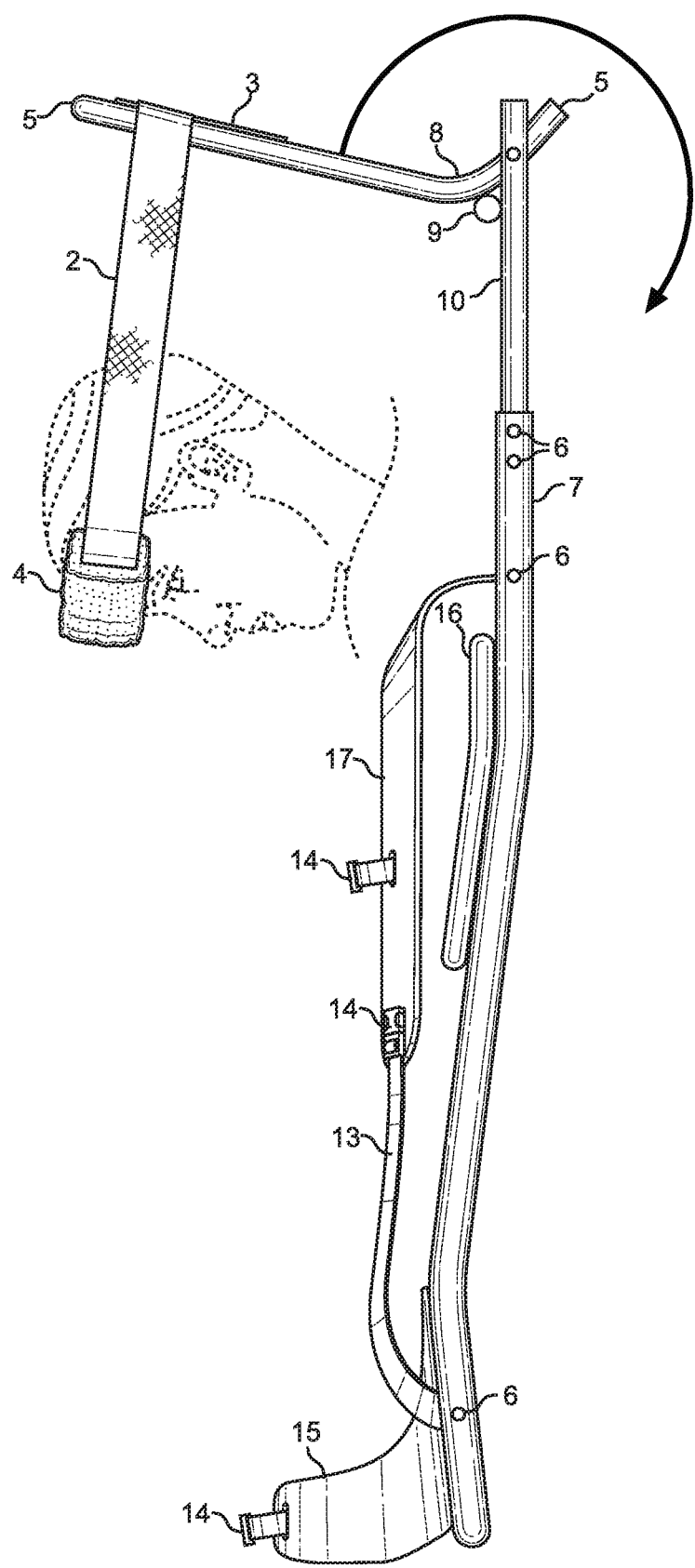
FIG. 7 illustrates a side view of the device of FIG. 6.

Shoulder harness 17 can be attached to the transverse bars with one or more of straps 13 and/or buckles 14. Securing member 7 can also be supported by the hips through hip belt 15, which can be secured with one or more of straps 13 and/or buckles 14. The attachment to the hips substantially stabilizes the device when a person's forehead is supported by the device. A pad 16 can also be attached to the transverse portion to increase comfort. The FIG. 7 illustrates a side view of the device of FIG. 6. A person places the forehead on padding 4 of strap 2. Ideally, a horizontal angle of zero degrees is obtained, but in some instances there may be an angle of less than 25 degrees depending on the person.

The upper ends of the two securing members 7 are configured to receive supporting member 1, such as with a male/female connection, and complementary openings for pins/fasteners.

The device is used by a user to support the head in a horizontal position. Securing member 7 is worn on the back of the user like a backpack with the help of backpack straps. The device positions the forehead strap with padding in front of the user in proximity to the chin level of the user. The user bends the head forwards the padding 4 and rests the forehead on the padding of the strap so that the weight of head is supported by the device.

When a person is standing erect, the distance between the lowest portion of the person's chin and the surface of strap 2 (measured without padding 4) where the forehead rests can be about 3 to 6 inches. The strap can be about 3 to 6 inches lower than the chin. Depending upon how the strap is adjusted, strap 2 can sit just under the chin or up to 5 inches out from the chin.

The devices can be folded substantially flat for optimal storage. The "L" beams (FIG. 1), which with the removal of the pins can be swiveled left/right to fold flat. For the devices of FIGS. 2-3, the fixed section, or "D" ring that supports the forehead restraining loop can be swiveled to the back to fold flat in line with the rest of the backpack frame for easy portability, flat storage, and shipping.

REFERENCE NUMBERS

1. Support (L-shaped)
2. Strap (hook and loop) entire strap is Velcro® (head strap made from hook & loop fastening material for easy attachment and adjustability)
3. Velcro® tape (hook & loop material to secure head strap and allow for adjustability)
4. Forehead rest (padding made preferably from soft material for comfort and grip)
5. End cap
6. Pin (fastener)
7. Securing member
8. Support (C, D or U-shaped)
9. Stopper (Cross Bar)
10. Support posts
11. Fastener
12. Pin (securing member) (fastener) (same as 6)
13. Adjustable straps
14. Slide release buckles
15. Padded hip belt
16. Back pad
17. Shoulder harness
18. Fastener (pin)
19. Adjustable support beam (has hook at end that can be put in different holes)
20. Hook
21. Openings for hook

What is claimed is:

1. A device for supporting a person's head in a horizontal position when the person is standing or walking or sitting in an erect position, comprising:
   A. A support member which is configured to attach to the person's body and configured to be positioned above the head;
   B. A head rest attached to the support member, the head rest is configured for a person to rest the person's forehead on with the head facing down in a horizontal position and the person's face looking at and parallel to the floor;
   C. The support member could take the shape of one or two "L" shaped bars, "D" shaped bars, "C" shaped bars or "U" shaped bars;
   D. A securing member that is configured to be positioned behind the person through which the support member is configured to be attached to the person's body, wherein the securing member comprises two bars that keep the support member in position, and;
   E. Two cross-bars connecting the two bars of the securing member to the support member, wherein each bar of the securing member has a plurality of openings configured to receive a hook at one end of each cross-bar.

\* \* \* \* \*